United States Patent [19]
Takahashi et al.

[11] Patent Number: 5,663,114
[45] Date of Patent: Sep. 2, 1997

[54] CATALYST FOR PRODUCTION OF PYROMELLITIC ANHYDRIDE AND METHOD FOR PRODUCTION OF PYROMELLITIC ANHYDRIDE

[75] Inventors: Tsukasa Takahashi; Tatsuya Kawabata; Masaaki Okuno; Yasuhisa Emoto; Yasushi Kiyooka; Kenji Ueda, all of Hyogo, Japan

[73] Assignee: Nippon Shokubai Co., Ltd., Osaka-fu, Japan

[21] Appl. No.: 327,234

[22] Filed: Oct. 21, 1994

[30] Foreign Application Priority Data

Oct. 22, 1993 [JP] Japan .................. 5-264757

[51] Int. Cl.$^6$ .................. B01J 23/50; B01J 23/22
[52] U.S. Cl. .................. 502/347; 502/305; 502/308; 502/309; 502/344; 502/350; 502/353
[58] Field of Search .................. 502/305, 308, 502/309, 312, 317, 344, 347, 350, 353; 549/239

[56] References Cited

U.S. PATENT DOCUMENTS

| | | | |
|---|---|---|---|
| 3,464,930 | 9/1969 | Friedrichsen et al. | 252/469 |
| 3,799,888 | 3/1974 | Suvoriv et al. | 252/469 |
| 4,414,412 | 11/1983 | De Alberti et al. | 562/235 |
| 4,537,874 | 8/1985 | Sato et al. | 502/311 |
| 4,665,200 | 5/1987 | Nakanishi et al. | 549/239 |
| 4,925,957 | 5/1990 | Enomoto et al. | 549/239 |
| 5,001,100 | 3/1991 | Enomoto et al. | 502/178 |
| 5,102,847 | 4/1992 | Yamamoto et al. | 502/209 |
| 5,206,201 | 4/1993 | Kishimoto et al. | 502/206 |
| 5,329,043 | 7/1994 | Matsuura et al. | 562/534 |
| 5,364,825 | 11/1994 | Neumann et al. | 502/311 |
| 5,420,091 | 5/1995 | Kuroda et al. | 502/209 |
| 5,470,815 | 11/1995 | Kim et al. | 502/304 |

FOREIGN PATENT DOCUMENTS

| | | | |
|---|---|---|---|
| 655686 | 1/1965 | Belgium . | |
| 1310229 | 1/1962 | France . | |
| 1156398 | 6/1958 | Germany . | |
| 4326497 | 7/1965 | Japan . | |
| 454978 | 7/1966 | Japan . | |
| 4515018 | 2/1967 | Japan . | |
| 4515252 | 3/1967 | Japan . | |
| 47338431 | 3/1968 | Japan . | |
| 4835251 | 9/1970 | Japan | C07C 63/32 |
| 4930821 | 11/1970 | Japan | C07C 63/32 |
| 4931972 | 11/1970 | Japan | C07C 63/32 |
| 4931973 | 12/1970 | Japan | C07C 63/32 |
| 01294679 | 2/1989 | Japan | C07D 493/04 |
| 1147554 | 6/1966 | United Kingdom | C07C 63/00 |
| 1156421 | 1/1967 | United Kingdom | C07C 51/32 |

OTHER PUBLICATIONS

European Search Report, EP 94 11 6714, Jan. 20, 1995.
"Heteropoly, Compounds of Mo and W", pp. 271–321.
"Mechanism of the Oxidation of o–Xylene to Phthalic Anhydride", pp. 531–539.
Journal of Catalysts 116, (1989).
Catalysis Reviews, vol. 19, pp. 269–321, (1987).
"Multicomponent Bismuth Molybdate Catalyst: A Highly Functonalized Catalyst System for the Selective Oxidation of Olefin", vol. 40, (1994) pp. 234–273.

*Primary Examiner*—Glenn A. Caldarola
*Assistant Examiner*—Alexander G. Ghyka
*Attorney, Agent, or Firm*—Omri M. Behr, Esq.

[57] ABSTRACT

A catalyst for obtaining pyromellitic anhydride at a high raw material gas concentration with high yield and a method for the production of pyromellitic anhydride are provided. The catalyst containing vanadium and silver as essential component elements for catalyst and having an atomic ratio of silver to vanadium in the range of from 0.001 to 0.2 allows efficient production of pyromellitic anhydride by the vapor-phase oxidation of a tetraalkylbenzene with a molecular oxygen-containing gas. The method of this invention accomplishes the production of pyromellitic anhydride by the use of the catalyst.

9 Claims, No Drawings

CATALYST FOR PRODUCTION OF PYROMELLITIC ANHYDRIDE AND METHOD FOR PRODUCTION OF PYROMELLITIC ANHYDRIDE

BACKGROUND OF THE INVENTION

1. Field of the Invention:

This invention relates to a catalyst for the production of pyromellitic anhydride and a method for the production of pyromellitic anhydride. More particularly, it relates to a catalyst to be used in the production of pyromellitic anhydride by the catalytic vapor-phase oxidation of a tetraalkylbenzene and a method for the production of pyromellitic anhydride from a tetraalkylbenzene by the use of the catalyst. The pyromellitic anhydride is extensively used as heat-resistant resins, plasticizers, epoxy resin-curing agents, etc. As an industrial raw material, it has been acquiring an increasingly great importance in recent years.

2. Description of the Prior Art:

Besides the method of catalytic vapor-phase oxidation of 1,2,4,5-tetramethylbenzene (occasionally referred to briefly as "durene"), a method which resorts to the liquid-phase oxidation of durene, a method which relies on the liquid-phase oxidation of 2,4,5-trimethylbenzaldehyde, and methods which reside in the synthesis of starting materials other than durene have been proposed for the production of pyromellitic anhydride. Among other methods cited above, the method of vapor-phase oxidation of durene has been particularly attracting attention as a process allowing inexpensive quantity production of pyromellitic anhydride because the raw material, durene, which has been heretofore expensive now promises to be inexpensively supplied in large quantities owing to the use of a zeolite type catalyst.

Numerous inventions covering catalysts for the catalytic vapor-phase oxidation of durene have been disclosed in patent literature. For example, a $V_2O_5$—$P_2O_5$—$TiO_2$, $MoO_3$, WO3 type catalyst (JP-B-45-4,978), a $V_2O_5$—$TiO_2$ anatase type)-$MoO_3$, $P_2O_5$ type catalyst (JP-B-45-15,018), a $V_2O_5$—$TiO_2$—$Na_2O$, $P_2O_5$ type catalyst (JP-B-45-15,252), a $V_2O_5$—$MoO_3$—$P_2O_5$ type catalyst (JP-B-47-38,431), a $V_2O_5$—$MoO_3$—$TiO_2$ type catalyst (JP-B-49-30,821), a $V_2O_5$—$TiO_2$—$P_2O_5$—$Nb_2O_5$—$K_2O$, CsO type catalyst (JP-A-49-31,972), a $V_2O_5$—$B_2O_3$—$SnO_2$, $P_2O_5$, $TiO_2$, $Na_2O$ type catalyst (JP-B-49-31,973), a $V_2O_5$—$B_2O_5$ type catalyst (JP-B-48-35,251), and a $V_2O_5$—$Na_2O$—$MoO_3$—Cr, Mn, Nb type catalyst (U.S. Pat. No. 4,925,957 and U.S. Pat. No. 5,001,100) have been disclosed.

The catalysts of these conventional compositions, however, hardly deserve to be called satisfactory from the commercial point of view because the concentration of a tetraalkylbenzene in the raw material gas composition is as low as less than 20 g/Nm³ and the pyromellitic acid aimed at is obtained only in an unduly low yield when this concentration is increased beyond 20 g/Nm³. None of the known catalysts contains silver as a component element. The effect of silver in the catalysis under consideration has never been known to the art.

A catalyst made of a vanadate which contains such a second metallic component as niobium, silver, molybdenum, chromium, or manganese has been known to be useful as a catalyst for the production of pyromellitic anhydride by the vapor-phase oxidation of durene with a molecular oxygen-containing gas (BP 1,147,554). This patent, however, only shows cases of using niobium vanadate and the per-pass yield of the operation involved is as low as about 46% by weight.

JP-B-43-26,497 discloses a catalyst formed of vanadium and niobium and intended for the production of pyromellitic anhydride by the vapor-phase oxidation of durene. The specification of this invention remarks in effect that this vanadium-niobium type catalyst may incorporate additionally therein such promoters as oxides, sulfates, or phosphates of alkali metals and alkaline earth metals, boron, silver, manganese or phosphorus, and antimony or arsenic. None of the working examples cited in this specification is found to embody the addition of such a promoter. Further, none of the operations demonstrating the use of the vanadium-niobium type catalyst is found to have given any sufficient yield.

An object of this invention, therefore, is to provide a novel catalyst for the production of pyromellitic anhydride by the catalytic vapor-phase oxidation of a tetraalkylbenzene.

Another object of this invention is to provide a novel method for the production of pyromellitic anhydride by the catalytic vapor-phase oxidation of a tetraalkylbenzene.

Yet another object of this invention is to provide a catalyst for producing pyromellitic acid efficiently with high yield in terms of commercial operation and a method for the production of pyromellitic anhydride.

Still another object of this invention is to provide a catalyst for producing pyromellitic anhydride at a high raw material gas concentration and with high yield and a method for the production of pyromellitic anhydride.

Yet still another object of this invention is to provide a product without color, to enhance high catching effect, and to attain synthetically high yield.

SUMMARY OF THE INVENTION

The objects mentioned above are accomplished by (1) a catalyst for the production of pyromellitic anhydride by the vapor-phase oxidation of a tetraalkylbenzene with a molecular oxygen-containing gas, characterized by containing vanadium and silver as essential component elements thereof and having an atomic ratio of silver to vanadium in the range of 0.001 to 0.2.

This invention further comprises the following factors.

(2) A catalyst according to the aforementioned factor (1), wherein the catalyst further comprises at least one second element selected from the group consisting of molybdenum and tungsten and the atomic ratio of the second element to vanadium is in the range of 0.01 to 2.

(3) A catalyst according to the aforementioned factor (1), wherein the catalyst further comprises at least one third element selected from the group consisting of phosphorus, antimony, boron, and cerium and the atomic ratio of the third element to vanadium is in the range of 0.001 to 1.

(4) A catalyst according to the aforementioned factor (3), wherein the third element is phosphorus.

(5) A catalyst according to the aforementioned factor (1), wherein the catalyst further comprises at least one fourth element selected from the group consisting of alkali metals, alkaline earth metals, and thallium and the atomic ratio of the fourth element to vanadium is in the range of 0.001 to 0.1.

(6) A catalyst according to the aforementioned factor (1), wherein the catalyst further comprises (a) at least one second element selected from the group consisting of molybdenum and tungsten and (b) at least one third element selected from the group consisting of phosphorus, antimony, boron, and cerium and the atomic ratio of the second element to vanadium is in the range of from 0.01 to 2 and the atomic ratio of the third element to vanadium is in the range of 0.001 to 1.

(7) A catalyst according to the aforementioned factor (1), wherein the catalyst further comprises (a) at least one second element selected from the group consisting of molybdenum and tungsten and (c) at least one fourth element selected from the group consisting of alkali metals, alkaline earth metals, and thallium and the atomic ratio of the second element to vanadium is in the range of from 0.01 to 2 and the atomic ratio of the fourth element to vanadium is in the range of 0.001 to 0.1.

(8) A catalyst according to the aforementioned factor (1), wherein the catalyst further comprises (b) at least one third element selected from the group consisting of phosphorus, antimony, boron, and cerium and (c) at least one fourth element selected from the group consisting of alkali metals, alkaline earth metals, and thallium and the atomic ratio of the third element to vanadium is in the range of from 0.001 to 1 and the atomic ratio of the fourth element to vanadium is in the range of 0.001 to 0.1.

(9) A catalyst according to the aforementioned factor (1), wherein the catalyst further comprises (a) at least one second element selected from the group consisting of molybdenum and tungsten, (b) at least one third element selected from the group consisting of phosphorus, antimony, boron, and cerium, and (c) at least one fourth element selected from the group consisting of alkali metals, alkaline earth metals, and thallium, the atomic ratio of the second element to vanadium is in the range of from 0.01 to 2, the atomic ratio of the third element to vanadium is in the range of from 0.001 to 1, and the atomic ratio of the fourth element to vanadium is in the range of 0.001 to 0.1.

(10) A catalyst according to any of the aforementioned factors (1) to (9), wherein the catalyst comprises addition of at least one oxide selected from the group consisting of titanium oxide, tin oxide, and zirconium oxide and the content of the oxide in terms of the surface area of the oxide per mol based on the total amount of the component elements is in the range of not less than 0 to not more than $1 \times 10^5$ m$^2$/mol.

(11) A catalyst according to any of the aforementioned factors (1) to (10), wherein the catalyst is in the form of granules having an average diameter in the range of 3 to 15 mm.

The aforementioned objects are further accomplished by (12) a method for the production of pyromellitic anhydride, characterized by subjecting a tetraalkylbenzene to vapor-phase oxidation with a molecular oxygen-containing gas in the presence of a catalyst according to any of the aforementioned factors (1) to (11).

This invention also contemplates (13) a method according to the factor (12), wherein the reaction temperature is in the range of 340° to 460° C. and the space velocity is in the range of 1000 to 15000 hr$^{-1}$. This invention further contemplates (14) a method according to the factor (12) or the factor (13), wherein the concentration of the tetraalkylbenzene in the molecular oxygen-containing gas is in the range of 10 to 60 g/Nm$^3$.

When the catalyst of the present invention is used in the production of pyromellitic anhydride by the vapor-phase oxidation of a tetraalkylbenzene, the yield of pyromellitic anhydride is exalted and the concentration in the raw material gas of the tetraalkylbenzene is allowed to be increased, and at the same time recovery ratio at the collection and purification steps can be increased by preventing the coloring of the product, therefore, the production is implemented at a high efficiency from the viewpoint of commercial operation.

EXPLANATION OF THE PREFERRED EMBODIMENT

In the catalyst of this invention, vanadium and silver are essential component elements for the construction of a catalyst. Action of silver resides in increase of catalytic activity and decrease of coloring components in the product, and increase of yield of pyromellitic anhydride by addition of an appropricate amount thereof. Generally, the atomic ratio of silver to vanadium is required to be in the range of 0.001 to 0.2. The contents of silver and vanadium in the catalyst, however, must be optimized in conformity with a variation in the composition of the other components of the catalyst. When the catalyst does not contain molybdenum and/or tungsten as an optional component element, the atomic ratio of silver to vanadium is desired to be selected in the range of 0.003 to 0.02. If silver is used in an unduly large amount, the excess will induce a sudden increase in the activity of combustion and entail a decline of the yield on the contrary. When the catalyst contains molybdenum and/or tungsten as an optional component element, the incorporation of silver therein proves to be particularly effective in implementing the production aimed at by this invention. The atomic ratio of silver to vanadium is desired to be selected in the range of 0.01 to 0.2, preferably in the range of from 0.02 to 0.1. Again in this case, the use of silver in an unduly large amount results in a decrease in the yield because the excess brings about a sharp increase in the activity of combustion. In the catalyst of this invention, the effect of the incorporation therein of silver is not fully manifested when the atomic ratio of silver to vanadium in the component elements of the catalyst is less than the lower limit of the range mentioned above. If the content of silver exceeds the upper limit of the range mentioned above, the excess will increase the amount of the combustion gas to be formed and entail a decrease in the yield. The exaltation of the yield of pyromellitic anhydride cannot be attained unless the content of silver in the catalyst is confined within the range mentioned above. Further, among the action of silver addition, prevention of coloring can be attained by over the above range.

When the product colors, in order to remove the color, it is necessary to purify or to catch it at a high temperature, but if the purification is carried out, the steps increase, so it causes not only increase of production cost but also generation of purification loss, as a result the yield decreases, so it is undesirable. And when the product is catched at high temperature, vapor pressure of pyromellitic anhydride becomes higher, so a content of pyromellitic anhydride in waste gas increases, so the yield sometimes decreases more than 5%. Therefore, it is very important requirement to obtain crystals without color and is worth to several mol % of increase of the yield.

As an optional component element of the catalyst of this invention, at least one second element to be selected from the group consisting of molybdenum and tungsten is used. The amount of the second element to be used is required to be such that the atomic ratio of the second element to vanadium may be in the range of 0.01 to 2, preferably in the range of 0.01 to 1, and more preferably in the range of 0.05 to 1. By having the second element incorporated as a component element in the catalyst in addition to silver, the selectivity of the reaction for pyromellitic anhydride can be improved and, when the second element is used in the range mentioned above, the pyromellitic anhydride can be produced with higher yield. If the second element is used in an amount exceeding the upper limit of the aforementioned range, the excess will lower the activity of catalysis, and at the same time the crystal becomes colored. If it is used in an amount less than the lower limit of the range, the effect of the addition thereof will be no longer discernible. Incidentally, when no silver is present as a component element in the catalyst, the addition of the second element in the range mentioned above rather has an adverse effect of impairing the activity of catalysis, encouraging the formation of by-products, preventing the yield from rising, and degrading the quality of the product.

Further, as an optional component element of the catalyst of this invention, at least one third element selected from the group consisting of phosphorus, antimony, boron, and cerium (hereinafter occasionally referred to as "element of A group") is used. As the element of A group, it is particularly desirable for the catalyst to contain at least phosphorus. The amount of the element of A group to be used is only required to be such that the atomic ratio of the element of A group to vanadium may be in the range of 0.001 to 1, preferably in the range of 0.01 to 1, and more preferably in the range of 0.02 to 0.5. The element of A group mainly functions to enhance the catalyst's selectivity. When it is used in a suitable amount in the catalyst, it curbs the occurrence of the combustion gas and improves the yield of pyromellitic anhydride. If it is used in an unduly large amount, the excess will aggravate the combustion and lower the yield of pyromellitic anhydride.

As yet another optional component element of the catalyst of this invention, at least one fourth element selected from the group consisting of alkali metals, alkaline earth metals, and thallium (hereinafter occasionally referred to as "element of B group") is used. The amount of the element of B group to be used is only required to be in the range of from 0.001 to 0.1, preferably in the range of 0.001 to 0.05, more preferably in the range of 0.001 to 0.01. An alkali and an alkaline earth metal as an element of B group affects the activity of catalysis. It improves both the activity and the selectivity when it is used in a small amount falling in the range mentioned above. The selectivity is lowered in proportion as this amount is increased. Both the selectivity and the activity are lowered when the amount is further increased.

Preferred embodiments of this invention are as follows.

(1) A catalyst produced by having a second element and a third element incorporated as additional component elements in the catalyst having vanadium and silver as essential component elements thereof. In this case, the atomic ratios of silver, the second element, and the third element respectively to vanadium are as described above.

(2) A catalyst produced by having a second element and a fourth element incorporated as additional component elements in the catalyst having vanadium and silver as essential component elements thereof. In this case, the atomic ratios of silver, the second element, and the fourth element respectively to vanadium are as described above.

(3) A catalyst produced by having a third element and a fourth element incorporated as additional component elements in the catalyst having vanadium and silver as essential component elements thereof. In this case, the atomic ratios of silver, the third element, and the fourth element respectively to vanadium are as described above.

(4) A catalyst produced by having a second element, a third element, and a fourth element incorporated as additional component elements in the catalyst having vanadium and silver as essential component elements thereof. In this case, the atomic ratios of silver, the second element, the third element, and the fourth element respectively to vanadium are as described above.

The optional component elements for the catalyst of this invention are desirable in respect that when the amounts thereof to be used are set at levels within the ranges mentioned above, the pyromellitic anhydride is obtained with high yield.

A further preferred embodiment of this invention consists in a catalyst which is obtained by causing at least one oxide selected from the group consisting of titanium oxide, tin oxide, and zirconium oxide to be additionally incorporated in the catalyst having the aforementioned composition and used for the production of pyromellitic anhydride. In this case, the production of pyromellitic anhydride is attained with high yield when the content of the oxide expressed in terms of the surface area of the oxide per mol based on the total amount of vanadium, silver, molybdenum, the element of A group, and the element of B group is in the range of not less than 0 to not more than $1 \times 10^5$ $m^2$/mol, preferably in the range of $1 \times 10^3$ to $1 \times 10^5$ $m^2$/mol. Particularly when the component elements of the catalyst mentioned above include molybdenum, the production of pyromellitic anhydride is obtained with high yield when the content of at least one oxide selected from the group consisting of titanium oxide, tin oxide, and zirconium oxide as expressed in terms of the surface area of the oxide per mol based on the total amount of vanadium, silver, molybdenum, the element of A group, and the element of B group in the component elements of the catalyst is selected especially in the range of $1 \times 10^3$ to $4 \times 10^4$ $m^2$/mol.

As the oxide, it is particularly preferable for the catalyst to contain at least titanium oxide. The incorporation of this oxide is desirable in respect that the oxide enables the activity of catalysis to be improved, the optimum reaction temperature to be lowered by not less than 10° C., and the selectivity to be enhanced. The expression "surface area ($m^2$/mol) of at least one oxide selected from the group consisting of titanium oxide, tin oxide, and zirconium oxide" as used herein means what is obtained by multiplying the weight (g) of the oxide used by the specific surface area ($m^2$/g) of the oxide and then dividing the resultant product by the total number of mols as metal of vanadium, silver, the second element, the element of A group, and the element of B group used in the catalyst. The specific surface area used in the calculation is determined by the Brunaer-Emmett-Teller (BET) method.

The method for preparing the catalyst and the raw material used therefor are not particularly limited. The catalyst can be prepared by any of the well-known methods heretofore employed popularly for the preparation of a catalyst. With respect to the silver as a component element, phosphates, nitrates, sulfates, lactates, citrates, and complex salts of silver can be used, for example. The other component elements of the catalyst are prepared by such raw materials as nitrates, carbonates, and organic salts of the relevant elements which are decomposed by heating into respective oxides. Then, titanium oxide, tin oxide, and zirconium oxide are prepared from the corresponding salts in advance of the preparation of the catalyst and then are fired so as to be used in the form of powdered oxides. They are used particularly advantageously when they have a surface area in the range of 5 to 100 $m^2$/g. For the sake of the preparation of the catalyst, these component elements are desired to be mixed as homogeneously as possible. The catalyst is manufactured by mixing or kneading the components of the catalyst of the composition mentioned above in a solvent such as, for example, water with the aid of a stirrer thereby forming a uniform liquid or slurry and depositing the liquid or the slurry on a carrier. At this time, for the purpose of enhancing the strength with which the catalyst is deposited on the carrier, a method which comprises mixing the liquid or the slurry with such a fibrous substance as whiskers can be adopted advantageously.

The carrier to be used herein may be any of the ordinary inert carriers heretofore in popular use. It is nevertheless desirable to use an inorganic porous carrier which has an apparent porosity in the range of 5 to 50% preferably from 10 to 40%, a specific surface area not exceeding 5 $m^2/g$, preferably falling in the range of 0.001 to 1 $m^2/g$, an aluminum content of not more than 10% by weight, preferably not more than 3% by weight, and a SiC content of not less than 50% by weight, preferably not less than 80% by weight. A self-sintering type porous carrier having a SiC purity of about 98% is also used advantageously.

The carrier is not particularly limited by shape. It may be in the form of granules shaped like spheres, rings, circular columns, cones, saddles, etc. A carrier having an average visible diameter in the approximate. range of 3 to 15 mm, preferably 3 to 10 mm, is conveniently used herein.

The deposition of the catalytically active substance on the carrier is implemented by any of the well-known methods such as, for example, the method of deposition by spraying and the method of deposition by impregnation. Preferably, this deposition of the catalytically active substance is accomplished by spraying the catalyst in the form of a solution or a slurry on the carrier kept at a temperature in the range of 150° to 350° C. The catalytically active substance is deposited in an amount in the range of 2 to 50 g, preferably 3 to 30 g, per 100 cc of the apparent volume of the carrier. The composite which is obtained by the deposition is calcined at a temperature in the range of 300° to 650° C., preferably 400° to 600° C., for a period in the range of 1 to 10 hours, preferably 2 to 6 hours, to complete the catalyst.

The catalyst of this invention formed as described above is packed in a reaction tube laid in a mass of heat medium such as fused salt kept at a prescribed temperature to prepare a fixed bed of catalyst. The pyromellitic anhydride aimed at is obtained by introducing a tetraalkylbenzene as a raw material into the fixed bed of catalyst and causing the raw material to undergo a catalytic vapor-phase oxidation therein with a molecular oxygen-containing gas.

As concrete examples of the tetraalkylbenzene to be used as the raw material, durene, ethylmethylbenzene, diethyldimethylbenzene, tetraethylbenzene, tetrapropylbenzene, and propyl-trimethylbenzene may be cited.

As respects the reaction conditions, the temperature of the heat medium is kept in the range of 340° to 460° C., preferably 370° to 440° C. If the temperature is higher than the upper limit of the range mentioned above, the combustion will be enlarged and the yield will be lowered. If the temperature is lower than the lower limit, the unaltered by-products will grow in quantity possibly to the extent of impairing the yield and degrading the quality of the product.

The reaction tube to be used herein has an inside diameter in the range of 15 to 40 mm, preferably 15 to 30 mm. The effectiveness of the removal of the heat of reaction grows in magnitude in proportion as the diameter of the reaction tube decreases. If this diameter is unduly small, however, the reaction tube will be at a disadvantage in obstructing the work of packing the catalyst therein.

The reaction gas is a mixture having a tetraalkylbenzene contained at a concentration in the range of 10 to 60 $g/Nm^3$, preferably 20 to 40 $g/Nm^3$, in a molecular oxygen-containing gas. If the concentration of the tetraalkylbenzene in the reaction gas is less than the lower limit of the range mentioned above, the productivity of the pertinent reaction will be unduly low and the practicability thereof will be nil. Conversely, if this concentration exceeds the upper limit of the range, the amount of the generated heat will be so large as to exert an adverse affect on the yield of the production and the service life of the catalyst.

Then, the concentration of oxygen in the molecular oxygen-containing gas to be used herein naturally must be high enough for the formation of pyromellitic anhydride from the tetraalkyl-benzene. Actually, the air can be used satisfactorily as the gas under consideration. As typical examples of the inert gas which may be contained in the molecular oxygen-containing gas besides the molecular oxygen, nitrogen, CO, $CO_2$, and rare gases may be cited.

The space velocity of the molecular oxygen-containing gas to be used for the reaction is in the range of 1000 to 15000 $hr^{-1}$, preferably 3000 to 10000 $hr^{-1}$. Any deviation of the space velocity from this range is undesirable. If this space velocity does not reach the lower limit of the range, then the combustion gas is generated in an unduly large amount. If it exceeds the upper limit, the amount of impurities entrained by the product is unduly large.

Now, this invention will be described more specifically below with reference to working examples.

The yields (mol%) of pyromellitic anhydride mentioned in the controls and the examples represent the magnitudes determined by liquid chromatography and reported as reduced to the values for the optimum reaction temperature ([Number of mols of formed pyromellitic anhydride/ Number of mols of supplied tetraalkyl benzene]×100).

The surface areas ($m^2/mol$) of at least one oxide selected from among titanium oxide, tin oxide, and zirconium oxide as mentioned in the controls and the examples represent the magnitudes obtained by multiplying the weights (g) of used oxides by the specific surface areas ($m^2/g$) of the oxides and dividing the resultant products by the total numbers (mol) of mols as metal of vanadium, silver, molybdenum, the element of A group, and the element of B group used in the catalysts. The specific surface areas of the oxides were determined by the BET method using an instrument (produced by Yuasa Ionix K.K. and marketed under trademark designation of "4-Sorb-US2") and nitrogen as an adsorbent gas.

As a titanium dioxide, $TiO_2$, an aqueous 7 wt% titanyl sulfate solution was hydrolyzed by boiling to produce hydrated titanium oxide in the form of a precipitate. This precipitate was thoroughly washed, fired at a temperature of 740° C. in a stream of air for 6 hours, and pulverized with a jet of air to produce an anatase type titanium dioxide powder having a specific surface area of 20 $m^2/g$. This powder was put to use.

EXAMPLE 1

In a solution of 560 g of oxalic acid in 1500 cc of purified water, 281 g of ammonium metavanadate and 16.6 g of ammonium dihydrogen phosphate were thoroughly stirred until the ensuant phenomenon of foaming vanished. The resultant solution, an aqueous 30 wt% silver nitrate solution added as $Ag_2O$ thereto in such an amount as to satisfy Ag/V (atomic ratio of silver to vanadium)=0.006, and 1.2 kg of titanium oxide with a specific surface area of 20 $m^2/g$ subsequently added thereto were mixed uniformly. The resultant mixture was diluted with purified water to prepare 4 liters of a catalyst slurry.

In an externally heated rotary furnace, 2000 cc of a self-sintering silicon carbide carrier of the form of spheres 4 mm in average particle diameter was preheated to a temperature in the range of 150° to 250° C. and the catalyst slurry prepared as described above was sprayed on the carrier to effect deposition of 150 g of the catalytic substance on the carrier. Then, in a calcination furnace, the composite having 150 g of the catalytic substance deposited on the carrier was calcined at 550° C. for 6 hours to obtain a catalyst X1. A reaction tube 20 mm in diameter was packed with the catalyst X1 in a length of 20 cm. A raw material gas having durene contained at a concentration of 20 g/Nm$^3$ in air was passed at a space velocity of 6000 hr$^{-1}$ through the reaction tube. The yield of the reaction was rated by passing the reaction gas through an air-cooled crystallizing vessel made of glass, collecting the gas emanating from the crystallizing vessel through two gas scrubbing bottles filled with purified water, dissolving the whole volume of the collected gas in purified water, and assaying the resultant aqueous solution for pyromellitic acid by liquid chromatography thereby determining the amount of pyromellitic anhydride produced. The yield of the pyromellitic anhydride was 58.7 mol% when the temperature of the molten salt bath was 390° C. The results are shown in Table 1.

CONTROL 1

A catalyst X21 was prepared by following the procedure of Example 1 while omitting the addition of silver. When the produced catalyst X21 was rated in the same manner as in Example 1, the yield of pyromellitic anhydride produced with the molten salt bath used at a temperature of 390° C. was found to be 58.0 mol%. The results are shown in Table 3.

EXAMPLE 2

In a solution of 2.4 kg of oxalic acid in 7000 cc of purified water, 1.2 kg of ammonium metavanadate, 180 g of ammonium molybdate, and 36.8 g of ammonium dihydrogen phosphate were stirred until the ensuant phenomenon of foaming vanished to produce a homogeneous solution. To the homogeneous solution no longer showing any sign of foaming, an aqueous 30 wt% silver nitrate solution was added as Ag$_2$O in such an amount as to satisfy Ag/V (atomic ratio)=0.05. The resultant mixed aqueous solution was diluted with purified water to prepare 9 liters of a catalyst slurry. In an externally heated rotary furnace, 2000 cc of a SiC carrier in the form of spheres 4 mm in average particle diameter was preheated to a temperature in the range of 280° to 330° C. and the catalyst slurry prepared as described above was sprayed on the SiC carrier to effect deposition of 100 g of a catalytic substance on the carrier. Then, in a calcination furnace, the composite having the catalytic substance deposited on the carrier was calcined at 500° C. for 6 hours to obtain a catalyst X2. A reaction tube 20 mm in diameter was packed with the catalyst X2 in a length of 20 cm. A raw material gas having durene contained at a concentration of 20 g/Nm$^3$ in air was passed at a space velocity of 6000 hr$^{-1}$ through the reaction tube.

The yield of pyromellitic anhydride was found to be 59.3 mol% when the temperature of the molten salt bath was 400° C.

The results are shown in Table 1. This yield is about 2 mol% higher than that obtained in Control 2 which corresponds to the present example.

CONTROL 2

A catalyst X22 was prepared by following the procedure of Example 2 while omitting the addition of silver. When the produced catalyst X22 was rated in the same manner as in Example 1, the yield of pyromellitic anhydride produced with the fused salt bath used at a temperature of 410° C. was found to be 57.2 mol%. The results are shown in Table 3.

EXAMPLE 3

In a solution of 2.4 kg of oxalic acid in 7000 cc of purified water, 1.2 kg of ammonium metavanadate, 180 g of ammonium molybdate, and 36.8 g of ammonium dihydrogen phosphate were stirred until the ensuant phenomenon of foaming vanished to produce a homogeneous solution. To the homogeneous solution no longer showing any sign of foaming, an aqueous 30 wt% silver nitrate solution was added as Ag$_2$O in such an amount as to satisfy Ag/V (atomic ratio)=0.04.

Then, the mixture consequently obtained and 2.6 kg of titanium oxide with a specific surface area of 20 m$^2$/g added thereto were uniformly mixed in an emulsifying vessel for 30 minutes. The uniform mixture thus obtained was diluted with purified water to prepare 9 liters of a catalyst slurry. In an externally heated rotary furnace, 2000 cc of a SiC carrier in the form of spheres 4 mm in average particle diameter was preheated to a temperature in the range of 280° to 330° C. and the catalyst slurry prepared as described above was sprayed on the SiC carrier to effect deposition of 100 g of a catalytic substance on the carrier. Then, in a calcination furnace, the composite having the catalytic substance deposited on the carrier was calcined at 500° C. for 6 hours to obtain a catalyst X3. When the catalyst X3 was rated in the same manner as in Example 1, the yield of the reaction was found to be 63.1 mol%. The results are shown in Table 1. This yield is about 2.5 mol% higher than that obtained in Control 3 which corresponds to the present example.

CONTROL 3

A catalyst X23 was prepared by following the procedure of Example 3 while omitting the addition of silver. When the produced catalyst X23 was rated in the same manner as in Example 1, the yield of pyromellitic anhydride produced with the fused salt bath used at a temperature of 395° C. was found to be 60.5 mol%. The results are shown in Table 3.

EXAMPLES 4 and 5

A catalyst X4 was obtained by following the procedure of Example 3 while changing the amount of silver nitride added so as to satisfy Ag/V=0.02 and a catalyst X5 was obtained by following the same procedure while changing the amount of silver nitride so as to satisfy Ag/V=0.1. When the catalyst X4 and the catalyst X5 were rated in the same manner as in Example 1, the yields of reaction were not less than 1.5 mol% higher than the yield obtained with the catalyst X21 containing no silver in spite of large changes in the optimum reaction temperature as shown in Table 1.

CONTROL 4

A catalyst X24 was prepared by following the procedure of Example 3 while changing the amount of silver nitrate added so as to satisfy Ag/V=0.3. When the produced catalyst X24 was rated in the same manner as in Example 1, the yield of pyromellitic anhydride produced with the fused salt bath used at a temperature of 370° C. was found to be 57.7 mol%. The results are shown in Table 3.

EXAMPLES 6 to 9

A catalyst X6 was prepared by following the procedure of Example 3 without addition of ammonium molybdate and a catalyst X7 by following procedure while changing the amount of ammonium molybdate added to satisfy Mo/V= 0.05, a catalyst X8 by following the same procedure while changing the amount of ammonium molybdate to satisfy Mo/V=0.3, and a catalyst X9 by following the same procedure while changing the amount of ammonium molybdate to satisfy Mo/V=1.0. These catalysts were used for the reaction under the same conditions as in Example 1.

As the result, the yields of reaction were found to be high as compared with the yield obtained in Control 3 which corresponds to the present example in spite of large changes caused in the optimum reaction temperature by changes in the amounts of molybdenum added as shown in Table 1.

EXAMPLE 10

A catalyst X10 was prepared by following the procedure of Example 5 while changing the amount of silver nitrate added so as to satisfy Ag/V=0.08.

When the produced catalyst X10 was rated in the same manner as in Example 1, the yield of pyromellitic anhydride produced with the fused salt bath used at a temperature of 400° C. was found to be 63.7 mol%. The results are shown in Table 1.

EXAMPLE 11

In a solution of 2.4 kg of oxalic acid in 7000 oc of purified water, 1.2 kg of ammonium metavanadate, 238 g of an aqueous ammonium metatungstate solution having a tungsten oxide content of 50% by weight, and 36.8 g of ammonium dihydrogen phosphate were thoroughly stirred until the ensuant phenomenon of foaming vanished.

To the homogeneous solution no longer showing any sign of foaming, an aqueous silver nitrate solution was added in such an amount as to satisfy Ag/V (atomic ratio)=0.05. The resultant mixed aqueous solution and 2.6 kg of titanium oxide with a specific surface area of 20 $m^2/g$ added thereto were uniformly mixed in an emulsifying device for 30 minutes. The resultant uniform mixture was diluted with purified water to prepare 9 liters of a catalyst slurry. In an externally heated rotary furnace, 2000 cc of a SiC carrier in the form of spheres 4 mm in average particle diameter was preheated to a temperature in the range of 280° to 330° C. and the catalyst slurry prepared as described above was sprayed on the SiC carrier to effect deposition of 100 g of a catalytic substance on the carrier. Then, in a calcination furnace, the composite having the catalytic substance deposited on the carrier was calcined at 500° C. for 6 hours to obtain a catalyst X11. When the produced catalyst X11 was rated in the same manner as in Example 1, the yield of pyromellitic anhydride produced with the molten salt bath used at a temperature of 390° C. was found to be 62.5 mol%. The results are shown in Table 1.

This yield is about 2 mol% higher than that obtained in Control 7 which corresponds to the present example. This fact indicates that the use of tungsten in the place of molybdenum produces an equal effect.

CONTROL 5

In a solution of 2.4 kg of oxalic acid in 7000 cc of purified water, 1.2 kg of ammonium metavanadate, 238 g of an aqueous ammonium metatungstate solution having a tungsten oxide content of 50% by weight, and 36.8 g of ammonium dihydrogen phosphate were thoroughly stirred until the ensuant phenomenon of foaming vanished. The resultant mixture and 2.6 kg of titanium oxide with a specific surface area of 20 $m^2/g$ added thereto were uniformly mixed in an emulsifying vessel for 30 minutes. The uniform mixture consequently obtained was diluted with purified water to prepare 9 liters of a catalyst slurry. In an externally heated rotary furnace, 2000 cc of a SiC carrier in the form of spheres 4 mm in average particle diameter was preheated to a temperature in the range of 280° to 330° C. and the catalyst slurry prepared as described above was sprayed on the carrier to effect deposition of 100 g of a catalytic substance on the carrier. Then, the composite having the catalytic substance deposited on the carrier was calcined in a calcination furnace at 500° C. for 6 hours to obtain a catalyst X25. When the produced catalyst X25 was rated in the same manner as in Example 1, the yield of pyromellitic anhydride produced with the molten salt bath used at a temperature of 400° C. was found to be 60.3 mol%. The results are shown in Table 3.

EXAMPLE 12

A catalyst X12 was prepared by following the procedure of Example 3 while changing the amount of ammonium dihydrogen phosphate added so as to satisfy P/V=0.1. When the produced catalyst X12 was rated in the same manner as in Example 1, the yield of pyromellitic anhydride produced with the molten salt bath used at a temperature of 400° C. was found to be 63 mol%. This yield is substantially equal to that obtained in Example 3. The results are shown in Table 1.

EXAMPLE 13

A catalyst X13 was prepared by following the procedure of Example 12 except that antimony pertoxide having a specific surface area of 52 $m^2/g$ was used instead of ammonium dihydrougen phosphate so as to become V/Sb=0.02. When the produced catalyst X13 was rated in the same manner as in Example 1, the yield of pyromellitic anhydride produced with fused molten bath used at a temperature of 390° C. was found to be 61.2 mol%. The results on shown in Table 1.

EXAMPLES 14 to 18

Catalysts X14, X15, X16, X17, and X18 were prepared by following the procedure of Example 3 while additionally using antimony, boron, cerium, calcium, and sodium respectively in such amounts as to satisfy the atomic ratios, Sb/V=0.006, B/V=0.2, Ce/V=0.001, Ca/V=0.006, and Na/V=0.002. These catalysts were rated in the same manner as in Example 1. The results are shown in Table 4.

The yields obtained with these catalysts were invariably not less than 2 mol% higher than those obtained with the respectively like catalysts X26, X27, X28, X29, and X30 which omitted addition of silver. Futher, these catalysts show higher yield than that of Example 3, so the addition of these elements brought higher yield.

As the sources for these additive elements, antimony pentoxide with a specific surface area of 52 $m^2/g$ was used for antimony, boric acid for boron, cerium oxide with a specific surface area of 33 $m^2/g$ for cerium, calcium nitrate for calcium, and sodium nitrate for sodium.

CONTROLS 6 to 10

A catalyst X26 was prepared by following the procedure of Example 14 while omitting the addition of silver, a catalyst X27 by following the procedure of Example 15 while omitting the addition of silver, a catalyst X28 by following the procedure of Example 16 while omitting the addition of silver, a catalyst X29 by following the procedure of Example 17 while omitting the addition of silver, and a catalyst X30 by following the procedure of Example 18 while omitting the addition of silver. These catalysts were rated in the same manner as in Example 1. The results are shown in Table 4.

EXAMPLE 19

A catalyst X19 was prepared by following the procedure of Example 6 while using silver phosphate as the source for silver and, at the same time, changing the amount of ammonium dihydrogen phosphate added so as to form a catalyst composition equivalent to that of the catalyst X15. The silver phosphate was used in its originally solid state. The catalyst X19 was rated in the same manner as in Example 1. The results are shown in Table 2.

EXAMPLE 20

The catalyst X17 prepared in Example 17 was rated by following the procedure of Example 1 while changing the durene gas concentration in the raw material gas to 30 g/Nm$^3$. As a result, pyromellitic anhydride was obtained at an yield of 63.0 mol%. This yield was higher than that obtained by using the like catalyst X23 containing no silver in the reaction using a durene concentration of 20 g/Nm$^3$. The results are shown in Table 2.

It is clearly noted from the comparison of the working examples with the controls cited above that in the production of pyromellitic anhydride, the yield of pyromellitic anhydride is higher when the catalyst used therein includes silver in the component elements of catalyst than when the catalyst contains no silver. The amount of silver to be incorporated in the catalyst is allowed to be increased particularly when the silver is added simultaneously with molybdenum or tungsten. As a result, the yield is exalted by not less than 2 mol%. The crystals collected in the crystallization tube assumed a color when the Mo/V atomic ratio was changed to 3.0. It is also clear from the results of Control 4 that when a catalyst containing silver as a component element thereof in an amount such that the atomic ratio of silver to vanadium exceeds 0.2 is used in the production of pyromellitic anhydride, the yield of pyromellitic anhydride is lower than when the catalyst contains no silver as a component element thereof.

TABLE 1

| | | Component element | | | | | Oxide | Reaction temperature | Yield of pyromellitic anhydride | Color of crystal |
|---|---|---|---|---|---|---|---|---|---|---|
| | Catalyst | V | Ag | Mo, W | A | B | (m$^2$/mol) | (°C.) | (mol %) | *3 |
| Example 1 | X 1 | 1 | 0.006 | — | P: 0.06 | — | TiO$_2$9400 | 390 | 58.7 | White |
| Example 2 | X 2 | 1 | 0.05 | Mo: 0.1 | P: 0.03 | — | — | 400 | 59.3 | White |
| Example 3 | X 3 | 1 | 0.04 | Mo: 0.1 | P: 0.03 | — | TiO$_2$4300 | 390 | 63.1 | White |
| Example 4 | X 4 | 1 | 0.02 | Mo: 0.1 | P: 0.03 | — | TiO$_2$4400 | 410 | 62.9 | White |
| Example 5 | X 5 | 1 | 0.1 | Mo: 0.1 | P: 0.03 | — | TiO$_2$4100 | 375 | 62.1 | White |
| Example 6 | X 6 | 1 | 0.04 | — | P: 0.03 | — | TiO$_2$4700 | 370 | 59.2 | White |
| Example 7 | X 7 | 1 | 0.04 | Mo: 0.05 | P: 0.03 | — | TiO$_2$4500 | 380 | 62.5 | White |
| Example 8 | X 8 | 1 | 0.04 | Mo: 0.3 | P: 0.03 | — | TiO$_2$3700 | 410 | 62.7 | White |
| Example 9 | X 9 | 1 | 0.04 | Mo: 1.0 | P: 0.03 | — | TiO$_2$4700 | 420 | 61.8 | White |
| Example 10 | X 10 | 1 | 0.08 | Mo: 0.3 | P: 0.03 | — | TiO$_2$3600 | 400 | 63.7 | White |
| Example 11 | X 11 | 1 | 0.04 | W: 0.05 | P: 0.03 | — | TiO$_2$4500 | 390 | 62.5 | White |
| Example 12 | X 12 | 1 | 0.04 | Mo: 0.1 | P: 0.1 | — | TiO$_2$4100 | 400 | 63 | White |
| Example 13 | X 13 | 1 | 0.04 | Mo: 0.1 | Sb: 0.02 | — | TiO$_2$4400 | 390 | 61.2 | White |

TABLE 2

| | | Component element | | | | | TiO$_2$ | Reaction temperature | Yield of pyromellitic anhydride | Color of crystal |
|---|---|---|---|---|---|---|---|---|---|---|
| | Catalyst | V | Ag | Mo, W | A | B | (m$^2$/mol) | (°C.) | (mol %) | *3 |
| Example 14 | X 14 | 1 | 0.04 | Mo: 0.1 | P: 0.03 Sb: 0.006 | — | TiO$_2$4300 | 395 | 63.8 | White |
| Example 15 | X 15 | 1 | 0.04 | Mo: 0.1 | P: 0.03 B: 0.2 | — | TiO$_2$3700 | 395 | 63.6 | White |
| Example 16 | X 16 | 1 | 0.04 | Mo: 0.1 | P: 0.03 Ce: 0.001 | — | TiO$_2$4300 | 390 | 63.4 | White |
| Example 17 | X 17 | 1 | 0.04 | Mo: 0.1 | P: 0.03 | Ca: 0.006 | TiO$_2$4300 | 390 | 63.9 | White |
| Example 18 | X 18 | 1 | 0.04 | Mo: 0.1 | P: 0.03 | Na: 0.002 | TiO$_2$4300 | 390 | 63.9 | White |
| Example 19 *1 | X 19 | 1 | 0.04 | Mo: 0.1 | P: 0.03 | Ca: 0.006 | TiO$_2$4300 | 390 | 64.2 | White |
| Example 20 *2 | X 17 | 1 | 0.04 | Mo: 0.1 | P: 0.03 | Ca: 0.006 | TiO$_2$4300 | 385 | 63 | White |

*1: Silver phosphate was used as the source for silver to be added.
*2: Concentration of raw material gas 30 g/Nm$^3$ (20 g/Nm$^3$ invariably in all the other working examples).
*3: Color of crystal collected by an air-cooling collecting tube.

Explanation of Table 1 and Table 2

In the column titled "Component element" of the tables, V stands for vanadium, Ag for silver, Mo. and W for at least one second element selected from the group consisting of molybdenum and tungsten, A for a third element, B for a fourth element, the oxide for at least one oxide selected from the group consisting of titanium oxide, tin oxide, and zirconium oxide, P for phosphorus, Sb for antimony, Ca for calcium, and Na for sodium.

In the rows covering data of controls, the numerals given in the columns for the component elements, V, Ag, Mo, and W represent atomic ratios of relevant elements and the column Mo. W is used for indicating which of the two elements is used in the relevant occasion. The columns of A and B are used for indicating names of elements and the atomic ratio of the elements and the column of oxide for indicating the kind of oxide and the surface area of the oxide per mol of the component elements of the catalyst.

indicating the kind of oxide and the surface area of the oxide per mol of the component elements of the catalyst.

What is claimed is:

1. A catalyst for the production of pyromellitic anhydride by the vapour phase oxidation of a tetraalkylbenzene with a molecular oxygen containing gas which comprises vanadium and silver in an atomic ratio of silver to vanadium in the range of 0.001 to 0.2, at least one member of the group consisting of molybdendum and tungsten wherein the atomic ratio of said group member to vanadium is in the range of 0.01 to 2 and at least one oxide selected from the group consisting of titanium oxide, and zirconium oxide, wherein the amount of said oxide in terms of surface area of said oxide per mole based on the total amount of said other components is in the range of $1 \times 10^3$ m$^2$/mol and $1 \times 10^5$ m$^2$/mol.

2. A catalyst according to claim 1, wherein said catalyst further comprises at least one component selected from the

TABLE 3

| | | | Component element | | | Oxide | Reaction temperature | Yield of pyromellitic anhydride | Color of crystal |
|---|---|---|---|---|---|---|---|---|---|
| | Catalyst | V | Ag | Mo, W | A | B | (m²/mol) | (°C.) | (mol %) | *1 |
| Control 1 | X 21 | 1 | — | — | P: 0.06 | — | TiO₂9400 | 390 | 58.0 | pale red |
| Control 2 | X 22 | 1 | — | Mo: 0.1 | P: 0.03 | — | — | 410 | 57.2 | red |
| Control 3 | X 23 | 1 | — | Mo: 0.1 | P: 0.03 | — | TiO₂4500 | 395 | 60.5 | red |
| Control 4 | X 24 | 1 | 0.3 | Mo: 0.1 | P: 0.03 | — | TiO₂3500 | 370 | 57.7 | White |
| Control 5 | X 25 | 1 | — | W: 0.05 | P: 0.03 | — | TiO₂4700 | 400 | 60.3 | orange |

TABLE 4

| | | | Component element | | | Oxide | Reaction temperature | Yield of pyromellitic anhydride | Color of crystal |
|---|---|---|---|---|---|---|---|---|---|
| | Catalyst | V | Ag | Mo, W | A | B | (m²/mol) | (°C.) | (mol %) | *1 |
| Control 6 | X 26 | 1 | — | Mo: 0.1 | P: 0.03 Sb: 0.006 | — | TiO₂4500 | 395 | 61.0 | red |
| Control 7 | X 27 | 1 | — | Mo: 0.1 | P: 0.03 B: 0.2 | — | TiO₂3800 | 400 | 60.6 | red |
| Control 8 | X 28 | 1 | — | Mo: 0.1 | P: 0.03 Ce: 0.001 | — | TiO₂4300 | 390 | 61.0 | red |
| Control 9 | X 29 | 1 | — | Mo: 0.1 | P: 0.03 | Ca: 0.006 | TiO₂4500 | 390 | 60.9 | pale red |
| Control 10 | X 30 | 1 | — | Mo: 0.1 | P: 0.03 | Na: 0.002 | TiO₂4500 | 390 | 60.9 | pale red |

*1: Color of crystol collected by an air-cooling collecting tube.

Explanation of Table 3 and Table 4

In the column titled "Component element" of the tables, V stands for vanadium, Ag for silver, Mo and W for at least one second element selected from the group consisting of molybdenum and tungsten, A for a third element, B for a fourth element, the oxide for at least one oxide selected from the group consisting of titanium oxide, tin oxide, and zirconium oxide, P for phosphorus, Sb for antimony, Ca for calcium, and Na for sodium.

In the rows covering data of controls, the numerals given in the columns for the component elements, V, Ag, Mo, and W represent atomic ratios of relevant elements and the column Mo or W is used for indicating which of the two elements is used in the relevant occasion. The columns of A and B are used for indicating names of elements and the atomic ratio of the elements and the column of oxide for group A consisting of phosphorus, antimony, boron, and cerium and the atomic ratio of said component to vanadium is in the range of 0.001 to 1.

3. A catalyst according to claim 2, wherein said group A component is phosphorus.

4. A catalyst according to claim 1, wherein said catalyst further comprises at least one component selected from the group B consisting of alkali metals, alkaline earth metals, and thallium and the atomic ratio of said component to vanadium is in the range of 0.001 to 0.1.

5. A catalyst according to claim 1, wherein said catalyst further comprises one group A component selected from the group consisting of phosphorus, antimony, boron, and cerium and the atomic ratio of said group A component to vandium is in the range of 0.001 to 1.

6. A catalyst according to claim 1, wherein said catalyst further comprises at least one group B component selected from the group consisting of alkali metals, alkaline earth metals, and thallium and the atomic ratio of said fourth element to vanadium is in the range of 0.001 to 0.1.

7. A catalyst according to claim 1, wherein said catalyst further comprises (b) at least one group A component selected from the group consisting of phosphorus, antimony, boron, and cerium and (c) at least one group B coponent selected from the group consisting of alkali metals, alkaline earth metals, and thallium and the atomic ratio of said group A component to vanadium is in the range of 0.001 to 1 and the atomic ratio of said group B component to vanadium is in the range of 0.001 to 0.1.

8. A catalyst according to claim 1, wherein said catalyst further comprises at least one group A component selected from the group consisting of phosphorus, antimony, boron, and cerium, and (c) at least one group B component selected from the group consisting of alkali metals, alkaline earth metals, and thallium, the atomic ratio of said group A component to vanadium is in the range of from 0.001 to 1, and the atomic ratio of said group B component to vanadium is in the range of 0.001 to 0.1.

9. A catalyst according to claim 1, wherein said catalyst is in the form of granules having an average diameter in the range of 3 to 15 mm.

* * * * *